United States Patent [19]

Willenbrock et al.

[11] 4,196,384

[45] Apr. 1, 1980

[54] PROBE ASSEMBLY FOR MONITORING LIQUIDS

[75] Inventors: Helmut Willenbrock, Achim; Friedrich Schittek, Bremen, both of Fed. Rep. of Germany

[73] Assignee: Gustav F. Gerdts KG, Bremen, Fed. Rep. of Germany

[21] Appl. No.: 883,542

[22] Filed: Mar. 6, 1978

[30] Foreign Application Priority Data

Mar. 12, 1977 [DE] Fed. Rep. of Germany ....... 2710872

[51] Int. Cl.² ............................................. G01N 27/42
[52] U.S. Cl. ...................................... 324/446; 324/438
[58] Field of Search ........................... 324/30 R, 30 B; 204/195 R

[56] References Cited

U.S. PATENT DOCUMENTS 2,611,007   9/1952   Cade et al. .......................... 324/30 B Primary Examiner—M. Tokar
Attorney, Agent, or Firm—Allison C. Collard; Thomas M. Galgano

[57] ABSTRACT

An improved probe assembly for monitoring liquids is provided which includes an electrode housing having an internal receiving chamber, sealing packing means disposed in the chamber and a generally cylindrical electrode enclosed within a flexible, tube-like insulation sheath, which electrode and sheath extend through the receiving chamber and the sealing packing means. The electrode has at least one circumferentially-extending, radially-offset surface disposed opposite the sealing packing means defining an edge against which the sheath is compressed by the packing means so as to effect sealing engagement between the electrode and the sheath.

4 Claims, 1 Drawing Figure

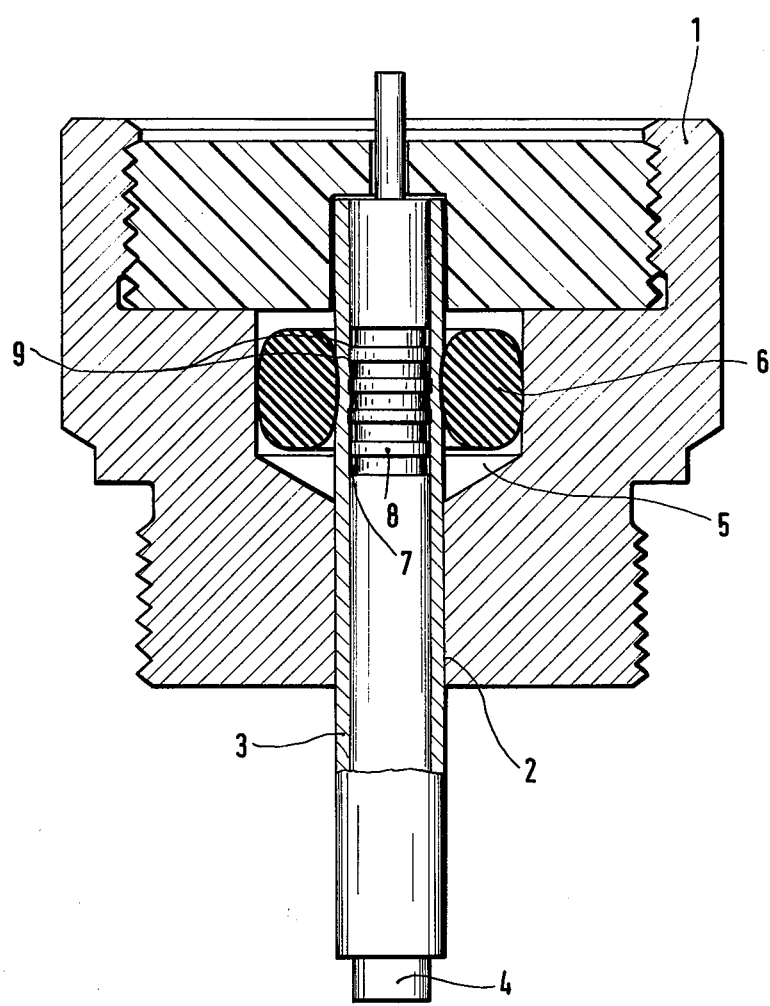

PROBE ASSEMBLY FOR MONITORING LIQUIDS

The present invention relates to a probe assembly for monitoring liquids. More particularly, it relates to an improved probe assembly for monitoring liquids of the type which includes an electrode housing having an internal receiving chamber, sealing packing means disposed in the chamber and a generally cylindrical electrode received within a plastic flexible tube-like sheath, which electrode and sheath extend through the receiving chamber and the sealing packing means.

With such probe assemblies and electrodes, it was heretofore not possible to obtain a constant pressure seal for the electrode passageway, since these types of electrodes are mainly employed, for example, for detecting the level of electrically conductive liquids and for controlling the conductivity of liquids. In particular, when the operating temperatures change, frequently a leak between the electrode and the surrounding insulation sheath or jackets occurs due to the creep tendency of the insulation sheath material.

It is, therefore, an object of the invention to provide a probe assembly of the aforementioned type, wherein a reliable seal is provided at the passageway for the electrode, even when the operating temperatures change.

The object of the invention is attained in accordance with the present invention by the provision of an improved probe assembly of the aforementioned type which is characterized by the provision of an electrode having at least one circumferentially-extending, radially-offset surface portion disposed opposite the sealing packing means which defines an edge against which the sheath is compressed by the packing means. This effects sealing engagement between the electrode and the sheath.

It had been found that by providing a circumferential compression edge against which the insulation sheath is pressed by the sealing packing means, a constant seal is obtained despite the creep tendency of the sheath material, even at changing operation temperatures.

Advantageously, the electrode is provided with a plurality of adjacent compression edges which permit especially large tolerances during the axial adjustment of the electrode and the seal packing means with respect to each other.

Most advantageously, the compression edges are defined by a plurality of circumferentially-extending, annular grooves provided on the electrode, which can be made quite easily. In this embodiment, the remaining shoulders or groove edges between the annular grooves provide the required compression edges and profiles. Such an electrode may be made from drawn rod material and only the annular grooves have to be milled in. The depths of the annular grooves are preferably less than the wall thickness of the insulation sheath to prevent undue and excessive compression of the insulation sheath.

Most desirably, the sealing packing means comprises an elastic ring which is provided with a radial pretension between the insulation sheath and the surrounding wall of the receiving chamber. Thereby, the ring provides the required sealing forces due to its elasticity and its inherited radial tension. As a result, special means for axial pressing of the sealing packing means are not required.

Other objects and features of the present invention will become apparent from the following detailed description when taken in connection with the accompanying drawing which discloses a single embodiment of the invention. It is to be understood that the drawing is designed for the purpose of illustration only, and is not intended as a definition of the limits and scope of the invention disclosed.

In the drawing, a cross-sectional view, in part elevation, of a novel probe assembly embodying the present invention is illustrated. Referring now, in detail to the drawing, an electrode housing 1 is provided having a longitudinal bore 2 through which an electrode 4 extends. Electrode 4 is received within a PTFE (polytetrafluoreythylene) insulation tube-like sheath or jacket 3. Within electrode housing 1, longitudinal bore 2 expands into a generally annular receiving chamber 5 in which is disposed an elastic sealing ring 6. The latter is inserted into the receiving chamber 5 with a radial pretension; i.e., the sealing ring 6 in its unassembled state has a larger outer diameter and a smaller inner diameter than the corresponding diameter of receiving chamber 5 and insulation sheath 3, respectively.

In the range of the sealing ring 6, electrode 4 is provided with a plurality of adjacent annular grooves 7, the depth of each of which is less than the wall thickness of insulation sheath 3. The shoulders 8 of electrode 4 which are defined between annular grooves 7, as well as the groove edges 9 provide compression edges or profiles at which locations insulation sheath 3 is compressed due to the effect of the radial tension of sealing ring 6. Thereby, a constant seal is obtained despite the creep tendency of the material of sheath 3 due to the changing temperatures. Thus, a tight seal between the insulation sheath 3 and the electrode 4 is provided in the same manner as it exists between insulation sheath 3, sealing ring 6 and electrode housing 1.

While only a single embodiment of the present invention has been shown and described, it will be obvious to those persons of ordinary skill in the art that many changes and modifications may be made thereunto without departing from the spirit and scope of the invention.

What is claimed is:

1. An improved probe assembly for monitoring liquids, comprising:
   an electrode housing having an internal receiving chamber;
   a substantially cylindrical electrode disposed in and extending through said chamber, said electrode having at least one circumferentially extending, radially-offset surface portion defining an edge;
   a resilient, insulating plastic sheath radially encompassing said electrode having an inner wall portion opposing said edge of said electrode; and
   an elastic sealing ring which is mounted with radial pretension between said insulating sheath and the surrounding wall of said receiving chamber, said sealing ring being disposed at a level adjacent to said edge of said electrode so that, as a result of its radial pretension, it biases said sheath against said edge of said electrode as a result of which a concentric radial sealing is effected between said sealing ring and said wall of said receiving chamber, said sealing ring and said sheath, and said sheath and said electrode, said radial sealing being induced solely by the radial pretension of said elastic sealing ring.

2. The probe assembly according to claim 1, wherein said electrode has a plurality of adjacent circumferentially-extending, radially-offset surface portions.

3. The probe assembly according to claim 1, wherein said electrode has at least one circumferentially-extending, annular groove which defines said radially-offset surface portion.

4. The probe assembly according to claim 3, wherein the depth of said annular groove is less than the wall thickness of said insulation sheath.

* * * * *